(12) United States Patent
Okada et al.

(10) Patent No.: US 9,494,881 B2
(45) Date of Patent: Nov. 15, 2016

(54) TRIARYLAMINE DERIVATIVE AND ELECTROPHOTOGRAPHIC PHOTOSENSITIVE MEMBER

(71) Applicant: KYOCERA Document Solutions Inc., Osaka (JP)

(72) Inventors: Hideki Okada, Osaka (JP); Fumio Sugai, Osaka (JP); Kensuke Kojima, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 14/953,190

(22) Filed: Nov. 27, 2015

(65) Prior Publication Data

US 2016/0179020 A1 Jun. 23, 2016

(30) Foreign Application Priority Data

Nov. 28, 2014 (JP) .................................. 2014-241216

(51) Int. Cl.
G03G 5/047 (2006.01)
G03G 5/06 (2006.01)
(Continued)

(52) U.S. Cl.
CPC ........... *G03G 5/0614* (2013.01); *C07C 211/54* (2013.01); *C07C 217/84* (2013.01)

(58) Field of Classification Search
CPC .................................................. G03G 5/0614
(Continued)

(56) References Cited

U.S. PATENT DOCUMENTS

2006/0147823 A1 7/2006 Kobayashi et al.

FOREIGN PATENT DOCUMENTS

JP 2004-252001 A 9/2004
JP 2006-008670 A 1/2006
(Continued)

OTHER PUBLICATIONS

Translation of JP 2006-126608.*
(Continued)

*Primary Examiner* — Peter Vajda
(74) *Attorney, Agent, or Firm* — Studebaker & Brackett PC

(57) ABSTRACT

A triarylamine derivative is represented by general formula (1) shown below.

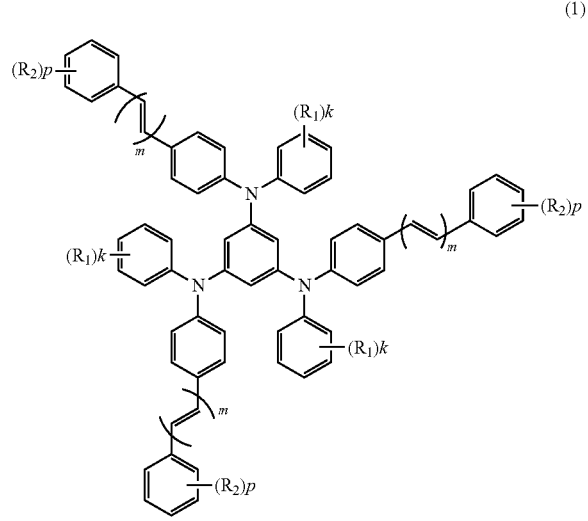

In general formula (1), each $R_1$ independently represents a halogen atom, an optionally substituted alkyl group having a carbon number of 1-6, an optionally substituted alkoxy (Continued)

group having a carbon number of 1-6, or an optionally substituted aryl group having a carbon number of 6-12. Each k independently represents an integer of 0-4, and each m independently represents an integer of 1-3. Each $R_2$ independently represents a halogen atom, an optionally substituted alkyl group having a carbon number of 1-6, an optionally substituted alkoxy group having a carbon number of 1-6, or an optionally substituted aryl group having a carbon number of 6-12. Each p independently represents an integer of 0-4.

12 Claims, 4 Drawing Sheets

(51) Int. Cl.
 *C07C 211/54* (2006.01)
 *C07C 217/84* (2006.01)
(58) Field of Classification Search
 USPC .......................................... 430/58.65, 58.75
 See application file for complete search history.

(56) References Cited

FOREIGN PATENT DOCUMENTS

| JP | 2006-126608 | * | 5/2006 | ............... G03G 5/06 |
| JP | 2007-121559 A | | 5/2007 | |
| JP | 2007-163523 A | | 6/2007 | |
| JP | 2009-007276 A | | 1/2009 | |
| JP | 4249730 B2 | | 4/2009 | |
| JP | 2010-037250 A | | 2/2010 | |

OTHER PUBLICATIONS

An Office Action; "Notice of Reasons for Rejection," issued by the Japanese Patent Office on Aug. 23, 2016, which corresponds to Japanese Patent Application No. 2014-241216 and is related to U.S. Appl. No. 14/953,190.

* cited by examiner

TRIARYLAMINE DERIVATIVE AND ELECTROPHOTOGRAPHIC PHOTOSENSITIVE MEMBER

INCORPORATION BY REFERENCE

The present application claims priority under 35 U.S.C. §119 to Japanese Patent Application No. 2014-241216, filed on Nov. 28, 2014. The contents of this application are incorporated herein by reference in their entirety.

BACKGROUND

The present disclosure relates to a triarylamine derivative and an electrophotographic photosensitive member in which the triarylamine derivative is used. More specifically, the present disclosure relates to a novel triarylamine derivative that is highly suitable for use as a hole transport material in an electrophotographic photosensitive member.

An electrophotographic photosensitive member used in an image forming apparatus or the like may, for example, be an organic photosensitive member made from organic photosensitive materials such as a charge transport material, a charge generating material, and a binder resin. An organic photosensitive member such as described above is easier to manufacture than an inorganic photosensitive member and also benefits from a high degree of structural design freedom due to the wide selection of photosensitive materials that is available.

Various compounds can be used as the hole transport material in the aforementioned organic photosensitive member. An amine stilbene derivative is particularly suitable as the hole transport material due to excellent charge transport ability.

SUMMARY

A first aspect of the present disclosure is a triarylamine derivative represented by general formula (1) shown below.

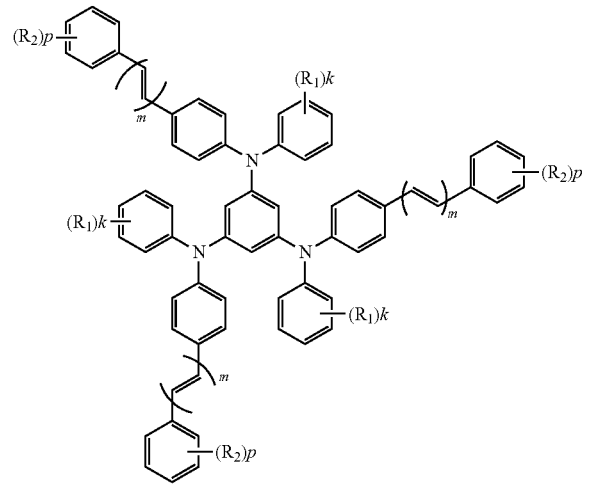

(1)

In general formula (1), each $R_1$ independently represents a halogen atom, an optionally substituted alkyl group having a carbon number of at least 1 and no greater than 6, an optionally substituted alkoxy group having a carbon number of at least 1 and no greater than 6, or an optionally substituted aryl group having a carbon number of at least 6 and no greater than 12. Each k independently represents an integer of at least 0 and no greater than 4, and each m independently represents an integer of at least 1 and no greater than 3.

In general formula (1), each $R_2$ independently represents a halogen atom, an optionally substituted alkyl group having a carbon number of at least 1 and no greater than 6, an optionally substituted alkoxy group having a carbon number of at least 1 and no greater than 6, or an optionally substituted aryl group having a carbon number of at least 6 and no greater than 12. Each p independently represents an integer of at least 0 and no greater than 4.

A second aspect of the present disclosure is an electrophotographic photosensitive member including a conductive substrate and a photosensitive layer. The photosensitive layer contains the triarylamine derivative according to the first aspect of the present disclosure.

DETAILED DESCRIPTION

Figure 1A:
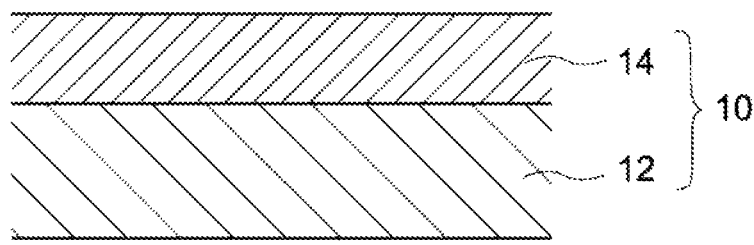
FIGS. 1A, 1B, and 1C each illustrate a single-layer electrophotographic photosensitive member according to an embodiment of the present disclosure.

The following explains embodiments according to the present disclosure. However, the present disclosure is not limited by the following embodiments.

First Embodiment

A first embodiment is a triarylamine derivative represented by general formula (1) shown below.

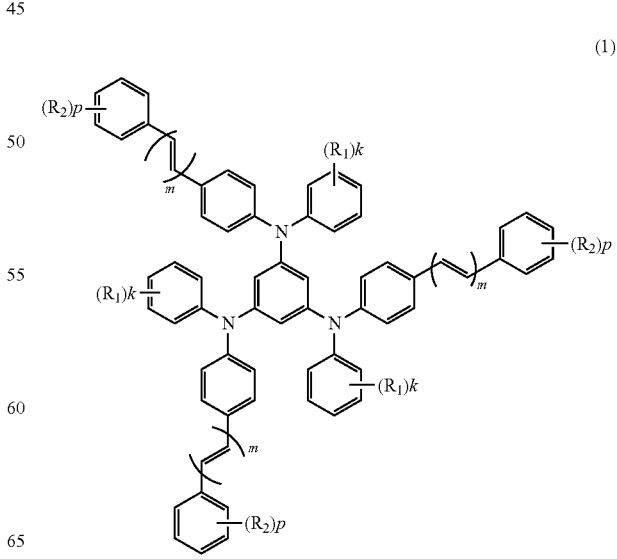

(1)

In general formula (1), each $R_1$ independently represents a halogen atom, an optionally substituted alkyl group having a carbon number of at least 1 and no greater than 6, an optionally substituted alkoxy group having a carbon number of at least 1 and no greater than 6, or an optionally substituted aryl group having a carbon number of at least 6 and no greater than 12. Each k independently represents an integer of at least 0 and no greater than 4, and each m independently represents an integer of at least 1 and no greater than 3.

In general formula (1), each $R_2$ independently represents a halogen atom, an optionally substituted alkyl group having a carbon number of at least 1 and no greater than 6, an optionally substituted alkoxy group having a carbon number of at least 1 and no greater than 6, or an optionally substituted aryl group having a carbon number of at least 6 and no greater than 12. Each p independently represents an integer of at least 0 and no greater than 4.

Examples of halogen atoms that may be represented by $R_1$ in general formula (1) include a fluorine atom, a chlorine atom, a bromine atom, and an iodine atom.

Examples of alkyl groups having a carbon number of at least 1 and no greater than 6 that may be represented by $R_1$ include a methyl group, an ethyl group, a propyl group, an isopropyl group, an n-butyl group, an isobutyl group, an s-butyl group, a t-butyl group, a pentyl group, an isopentyl group, a neopentyl group, and a hexyl group. The carbon number of the alkyl group is preferably at least 1 and no greater than 4, and more preferably at least 1 and no greater than 3. The alkyl group may have one or more substituents. Examples of possible substituents include alkyl groups.

Alkoxy groups having a carbon number of at least 1 and no greater than 6 that may be represented by $R_1$ include a methoxy group, an ethoxy group, an n-propoxy group, an isopropoxy group, an n-butoxy group, an isobutoxy group, an s-butoxy group, a t-butoxy group, a pentyloxy group, an isopentyloxy group, a neopentyloxy group, and a hexyloxy group. The carbon number of the alkoxy group is preferably at least 1 and no greater than 4, and more preferably at least 1 and no greater than 3. The alkoxy group may have one or more substituents. Examples of possible substituents include alkyl groups.

Examples of aryl groups having a carbon number of at least 6 and no greater than 12 that may be represented by $R_1$ include a phenyl group, a tolyl group, a xylyl group, a biphenylyl group, an o-terphenyl group, a naphthyl group, an anthryl group, and a phenanthryl group. The aryl group may have one or more substituents, and preferably has at least one and no greater than three substituents. Examples of possible substituents include alkyl groups, aralkyl groups, alkoxy groups, alkanoyl groups, halogen atoms, and alkoxycarbonyl groups.

Each k represents an integer of at least 0 and no greater than 4, and preferably represents an integer of at least 1 and no greater than 3. When k represents an integer greater than 1, each corresponding $R_1$ may be the same or different to one another.

Each m represents an integer of at least 1 and no greater than 3, and preferably represents 2 or 3.

In general formula (1), each $R_2$ independently represents a halogen atom, an optionally substituted alkyl group having a carbon number of at least 1 and no greater than 6, an optionally substituted alkoxy group having a carbon number of at least 1 and no greater than 6, or an optionally substituted aryl group having a carbon number of at least 6 and no greater than 12. Each p independently represents an integer of at least 0 and no greater than 4.

Examples of halogen atoms that may be represented by $R_2$ in general formula (1) include a fluorine atom, a chlorine atom, a bromine atom, and an iodine atom.

Examples of alkyl groups having a carbon number of at least 1 and no greater than 6 that may be represented by $R_2$ include a methyl group, an ethyl group, a propyl group, an isopropyl group, an n-butyl group, an isobutyl group, an s-butyl group, a t-butyl group, a pentyl group, an isopentyl group, a neopentyl group, and a hexyl group. The carbon number of the alkyl group is preferably at least 1 and no greater than 4, and more preferably at least 1 and no greater than 3. The alkyl group may have one or more substituents. Examples of possible substituents include alkyl groups.

Examples of alkoxy groups having a carbon number of at least 1 and no greater than 6 that may be represented by $R_2$ include a methoxy group, an ethoxy group, an n-propoxy group, an isopropoxy group, an n-butoxy group, an isobutoxy group, an s-butoxy group, a t-butoxy group, a pentyloxy group, an isopentyloxy group, a neopentyloxy group, and a hexyloxy group. The carbon number of the alkoxy group is preferably at least 1 and no greater than 4, and more preferably at least 1 and no greater than 3. The alkoxy group may have one or more substituents. Examples of possible substituents include alkyl groups.

Examples of aryl groups having a carbon number of at least 6 and no greater than 12 that may be represented by $R_2$ include a phenyl group, a tolyl group, a xylyl group, a biphenylyl group, an o-terphenyl group, a naphthyl group, an anthryl group, and a phenanthryl group. The aryl group may have one or more substituents, and preferably has at least one and no greater than three substituents. Examples of possible substituents include alkyl groups, aralkyl groups, alkoxy groups, alkanoyl groups, halogen atoms, and alkoxycarbonyl groups.

Each p represents an integer of at least 0 and no greater than 4, and preferably represents an integer of at least 1 and no greater than 3. When p represents an integer greater than 1, each corresponding $R_2$ may be the same or different to one another.

The triarylamine derivative represented by general formula (1) shown above has a three dimensional conjugated structure and consequently has excellent solvent solubility and binder resin compatibility. Therefore, in a situation in which the triarylamine derivative described above is used as a charge transport material (hole transport material) in an electrophotographic photosensitive member, the triarylamine derivative can be uniformly dispersed in a photosensitive layer of the electrophotographic photosensitive member and the electrophotographic photosensitive member can be provided with excellent sensitivity properties. An electrophotographic photosensitive member according to the present disclosure can contribute to improving speed and performance of various image forming apparatuses such as copiers and printers.

Preferable examples of the triarylamine derivative represented by general formula (1) include triarylamine derivatives HT-1 to HT-6 shown below.

HT-1
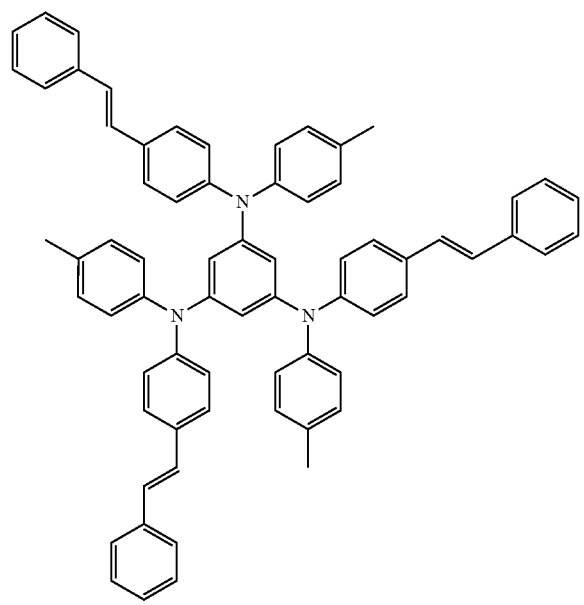
HT-3
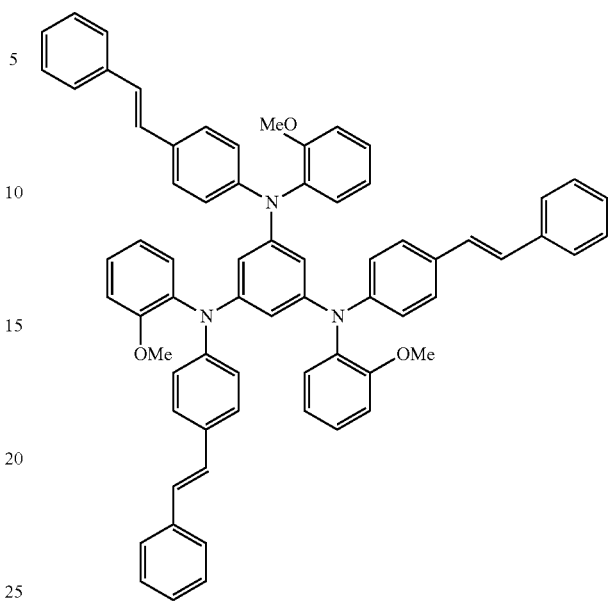
HT-2
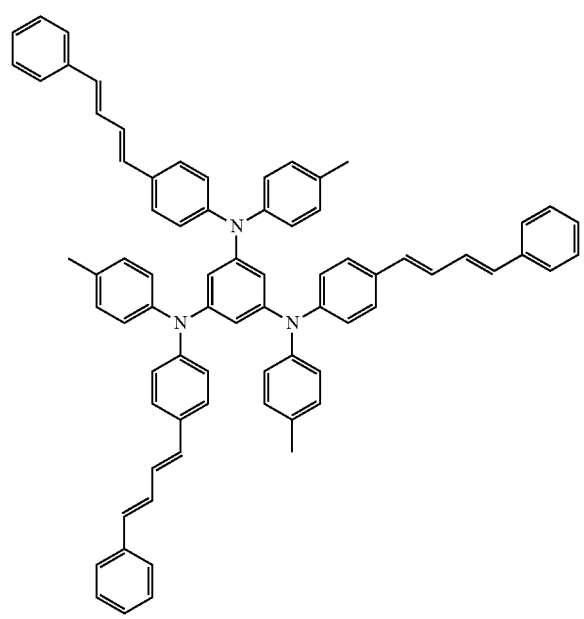
HT-4
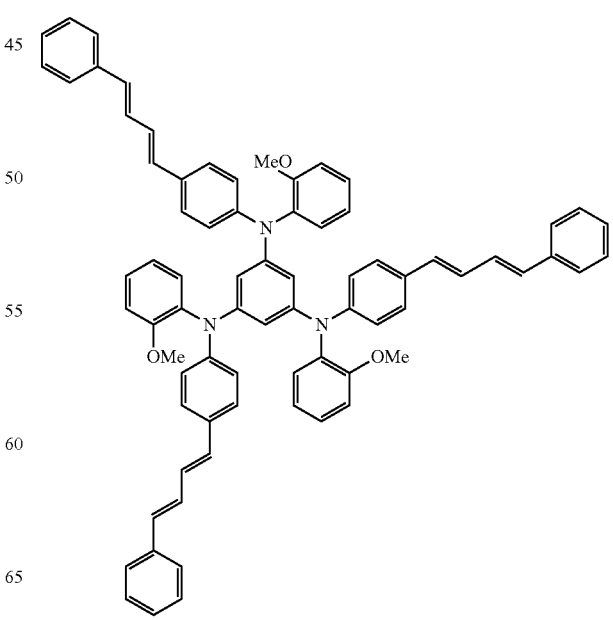

-continued

HT-5

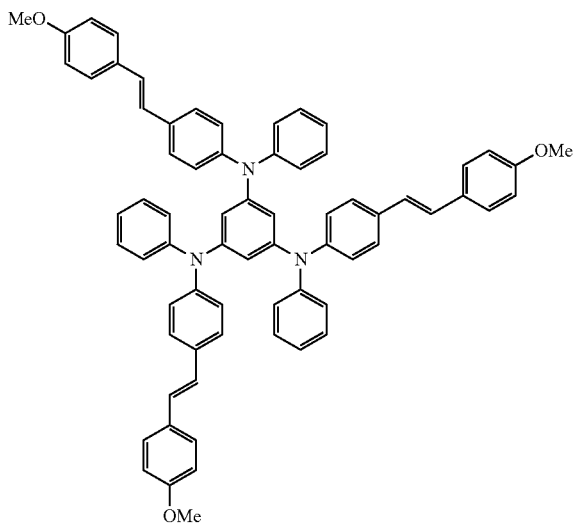

HT-6

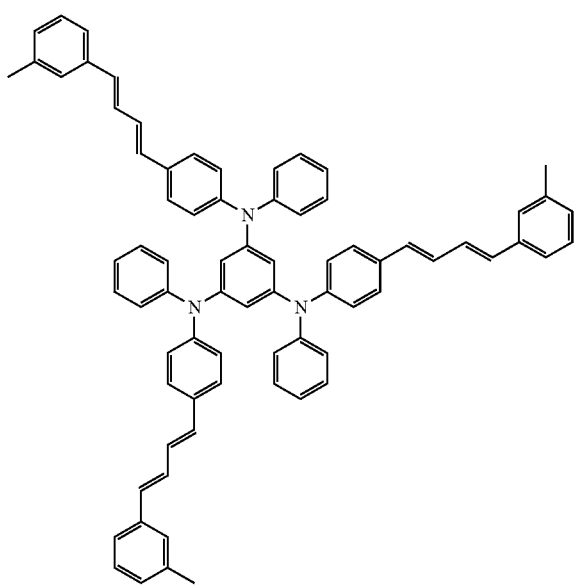

The following explains a method for manufacturing the triarylamine derivative represented by general formula (1).

Specific explanation of methods for manufacturing the triarylamine derivatives HT-1 to HT-6 is provided in synthesis examples 1-6 of the Examples.

The following explains a method for manufacturing the triarylamine derivative HT-1.

[Synthesis of Triarylamine Derivative HT-1]

The triarylamine derivative HT-1 can be manufactured by carrying out a two stage coupling reaction represented by reaction formula (1) shown below.

Reaction formula (1)

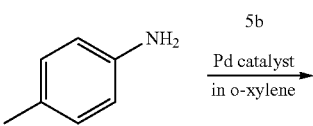

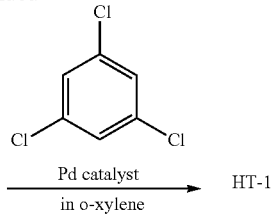

(First Coupling Reaction: Intermediate Synthesis)

A reaction ratio (molar ratio) of compound 5b and p-toluidine is preferably in a range of 5:1 to 1:1, and more preferably in a range of 2:1 to 1:1.

Note that the compound 5b can be manufactured in accordance with a synthetic example in the Examples.

The reaction is preferably carried out at a reaction temperature of at least 80° C. and no greater than 140° C. and with a reaction time of at least 2 hours and no greater than 10 hours.

A palladium compound is preferably used as a catalyst. The reason for preferably using a palladium compound as a catalyst is that the palladium compound can improve the percentage yield of the triarylamine derivative HT-1.

Examples of palladium compounds that can be used include tetravalent palladium compounds such as hexachloro palladium(IV) sodium tetrahydrate and hexachloro palladium(IV) potassium tetrahydrate, divalent palladium compounds such as palladium(II) chloride, palladium(II) bromide, palladium(II) acetate, palladium(II) acetylacetate, dichlorobis(benzonitrile)palladium(II), dichlorobis(triphenylphosphine)palladium(II), dichlorotetramine palladium(II), and dichloro(cycloocta-1,5-diene) palladium(II), and other palladium compounds such as tris (dibenzylideneacetone)dipalladium(0), tris (dibenzylideneacetone)dipalladium(0) chloroform complex, and tetrakis(triphenylphosphine)palladium(0). Any one type of catalyst may be used or a combination of any two or more types of catalysts may be used.

The additive amount of the palladium compound is preferably at least 0.0005 mol and no greater than 20 mol relative to 1 mol of the compound 5b, and more preferably at least 0.001 mol and no greater than 1 mol.

The first coupling reaction is preferably carried out in the presence of a base. The reason for preferably carrying out the first coupling reaction in the presence of a base is that hydrogen halide (hydrogen chloride) produced in the reaction can be rapidly neutralized and that, as a result, catalytic activity can be improved and the percentage yield of the triarylamine derivative HT-1 can be further improved.

A base selected from among inorganic bases and organic bases can be used. Although no particular limitations are placed on the base, preferable examples include alkali metal alkoxides such as sodium methoxide, sodium ethoxide, potassium methoxide, potassium ethoxide, lithium tert-butoxide, sodium tert-butoxide, and potassium tert-butoxide, with sodium tert-butoxide being particularly preferable. Examples of effective inorganic bases include tripotassium phosphate and cesium fluoride.

A preferable additive amount of the base is dependent on the additive amount of the palladium compound. For example, in a situation in which 0.005 mol of the palladium compound is added relative to 1 mol of the compound 5b, the additive amount of the base is preferably at least 1 mol and no greater than 10 mol, and more preferably at least 1 mol and no greater than 5 mol.

Examples of solvents that can be used in the first coupling reaction include xylene, toluene, tetrahydrofuran, and dimethyl formamide.

[Second Coupling Reaction: Synthesis of Triarylamine Derivative HT-1]

A reaction ratio (molar ratio) of the intermediate and trichlorobenzene is preferably in a range of 5:1 to 2:1, and more preferably a range of 4:1 to 3:1.

The second coupling reaction is preferably carried out at a reaction temperature of at least 80° C. and no greater than 140° C. and with a reaction time of at least 2 hours and no greater than 10 hours.

A palladium compound is preferably used as a catalyst. Examples of palladium compounds that can be used are the same as for the first coupling reaction. Furthermore, a preferable additive amount of the palladium compound is the same as for the first coupling reaction.

The second coupling reaction is preferably carried out in the presence of a base. Examples of bases that can be used are the same as for the first coupling reaction. Furthermore, a preferable additive amount of the base is the same as for the first coupling reaction.

Examples of solvents that can be used in the second coupling reaction are the same as for the first coupling reaction.

The triarylamine derivative synthesized as described above is highly suitable for use as a hole transport material in a photosensitive layer of an electrophotographic photosensitive member and can also be used in various other technical fields such as solar cells and electroluminescent elements.

Second Embodiment

A second embodiment is an electrophotographic photosensitive member including a conductive substrate and a photosensitive layer that contains the triarylamine derivative represented by general formula (1).

Specific explanation of the second embodiment is provided below by focusing on points that differ from the description of the first embodiment.

An electrophotographic photosensitive member is typically a single-layer electrophotographic photosensitive member (also referred to as single-layer photosensitive member) or a multi-layer electrophotographic photosensitive member (also referred to as a multi-layer photosensitive member). The triarylamine derivative according to the present disclosure can be adopted in either of the above types of electrophotographic photosensitive members.

However, adoption in a single-layer electrophotographic photosensitive member is preferable for reasons such as, in particular, applicability to both negatively and positively charging photosensitive members, simple structure and ease of manufacture, effective inhibition of film defects in photosensitive layer formation, and improved optical properties due to a small number of interfaces between layers.

<<Single-Layer Electrophotographic Photosensitive Member>>

(Basic Configuration)

As illustrated in FIG. 1A, a single-layer electrophotographic photosensitive member 10 includes a single photosensitive layer 14 on a conductive substrate 12.

The photosensitive layer can for example be formed by dissolving or dispersing the triarylamine derivative represented by general formula (1) (hole transport material), a charge generating material, a binder resin, and, depending on necessity, an electron transport material in an appropriate solvent, applying a resultant application liquid onto a conductive substrate, and drying the application liquid thereon.

The single-layer electrophotographic photosensitive member can be used as either a positively or negatively charging type through a single configuration, has a simple layer structure, and is easy to manufacture.

In addition, the single-layer electrophotographic photosensitive member has excellent sensitivity through inclusion of the triarylamine derivative represented by general formula (1). In a situation in which the photosensitive layer of the single-layer electrophotographic photosensitive member further contains an electron transport material, electron exchange between the charge generating material and the hole transport material tends to occur efficiently and sensitivity tends to be more stabilized.

(Conductive Substrate)

Examples of various conductive materials that can be used as the conductive substrate include metals such as iron, aluminum, copper, tin, platinum, silver, vanadium, molybdenum, chromium, cadmium, titanium, nickel, palladium, indium, stainless steel, and brass, plastic materials onto which any of the aforementioned metals are laminated or applied by vapor deposition, and glass coated with aluminum iodide, tin oxide, indium oxide, or the like.

The conductive substrate has a shape such as a sheet shape or a drum shape that matches the structure of an image forming apparatus in which the conductive substrate is used. The conductive substrate may be a substrate that is itself conductive or may be a substrate having a conductive surface layer. The conductive substrate preferably has sufficient mechanical strength during use.

(Charge Generating Material)

Examples of charge generating materials that can be used include metal-free phthalocyanine (τ-form or X-form), titanyl phthalocyanine (α-form or Y-form), hydroxygallium phthalocyanine (V-form), and chlorogallium phthalocyanine (II-form). Any one type of charge generating material may be used or a combination of any two or more types of charge generating materials may be used. In a configuration in which a hole transport material and an electron transport material are used in combination, an electrophotographic photosensitive member having excellent sensitivity properties, electrical properties, and stability can be provided through appropriate specification of the type of charge generating material used.

Preferably a commonly known charge generating material is used individually or in combination. Examples of types of charge generating materials that can be used include organic photoconductive materials such as phthalocyanine-based pigments (for example, titanyl phthalocyanine), perylene-based pigments, bisazo pigments, diketopyrrolopyrrole pigments, metal-free naphthalocyanine pigments, metal naphthalocyanine pigments, squaraine pigments, tris-azo pigments, indigo pigments, azulenium pigments, cyanine pigments, pyrylium pigments, anthanthrone pigments, triphenylmethane-based pigments, threne pigments, toluidine-based pigments, pyrazoline-based pigments, and quinacridone-based pigments, and inorganic photoconductive materials such as selenium, selenium-tellurium, selenium-arsenic, cadmium sulfide, and amorphous silicon. Any one of the above types may be used or a combination of any two or more of the above types may be used.

In a digital optical image forming apparatus, such as a laser beam printer or facsimile machine, that includes a semiconductor laser or the like as a light source, the image forming apparatus requires a photosensitive member that is sensitive to light in a region of wavelengths greater than 700 nm Therefore, among the charge generating materials listed above, one or more of metal-free phthalocyanine, titanyl phthalocyanine, hydroxygallium phthalocyanine, and chlorogallium phthalocyanine are preferably used in such an image forming apparatus.

On the other hand, a perylene-based pigment or a bisazo pigment is for example suitable in the case of an analog optical image forming apparatus, such as an electrostatic copier, that includes a halogen lamp as a white light source because the image forming apparatus requires a photosensitive member that is sensitive to light in the visible region.

(Hole Transport Material)

The electrophotographic photosensitive member according to the present disclosure preferably contains the triarylamine derivative represented by general formula (1) as a hole transport material. Note that the photosensitive layer may contain a commonly known hole transport material in addition to the triarylamine derivative.

Examples of commonly known hole transport materials that can be used include oxadiazole-based compounds such as 2,5-di(4-methylaminophenyl)-1,3,4-oxadiazole, styryl-based compounds such as 9-(4-diethylaminostyryl)anthracene, carbazole-based compounds such as polyvinyl carbazole, organic polysilane compounds, pyrazoline-based compounds such as 1-phenyl-3-(p-dimethylaminophenyl) pyrazoline, nitrogen containing cyclic compounds such as hydrazone-based compounds, triphenyl amine-based compounds, indole-based compounds, oxazole-based compounds, isoxazole-based compounds, thiazole-based compounds, thiadiazole-based compounds, imidazole-based compounds, pyrazole-based compounds, and triazole-based compounds, and condensed polycyclic compounds. Any one type of hole transport material may be used or a combination of any two or more types of hole transport materials may be used.

(Electron Transport Material)

Examples of electron transport materials that can be used include quinone derivatives, anthraquinone derivatives, malononitrile derivatives, thiopyran derivatives, trinitrothioxanthone derivatives, 3,4,5,7-tetranitro-9-fluorenone derivatives, dinitroanthracene derivatives, dinitroacridine derivatives, nitroanthraquinone derivatives, dinitroanthraquinone derivatives, tetracyanoethylene, 2,4,8-trinitrothioxanthone, dinitrobenzene, dinitroanthracene, dinitroacridine, nitroanthraquinone, dinitroanthraquinone, succinic anhydride, maleic anhydride, and dibromomaleic anhydride. Any one type of electron transport material may be used or a combination of any two or more types of electron transport materials may be used.

(Binder Resin)

A binder resin used to disperse the charge generating material may for example be a thermoplastic resin, a thermosetting resin, or a photocurable resin. Examples of thermoplastic resins that can be used include polycarbonate resins such as bisphenol Z, bisphenol ZC, bisphenol C, and bisphenol A type polycarbonate resins, polyarylate resins, styrene-butadiene copolymers, styrene-acrylonitrile copolymers, styrene-maleate copolymers, acrylic copolymers, styrene-acrylate copolymers, polyethylene resins, ethylene-vinyl acetate copolymers, chlorinated polyethylene resins, polyvinyl chloride resins, polypropylene resins, ionomer resins, vinyl chloride-vinyl acetate copolymers, alkyd resins, polyamide resins, polyurethane resins, polysulfone resins, diallyl phthalate resins, ketone resins, polyvinyl butyral resins, and polyether resins. Examples of thermosetting resins that can be used include silicone resins, epoxy resins, phenolic resins, urea resins, melamine resin, and other crosslinkable thermosetting resins. Examples of photocurable resins that can be used include epoxy acrylate and urethane acrylate. Any one type of binder resin may be used or a combination of any two or more types of binder resins may be used.

(Additives)

In addition to each of the components described above, the photosensitive layer may contain various commonly known additives to the extent that such additives do not adversely affect electrophotographic properties of the photosensitive layer. Examples of additives that may be used include antidegradants such as antioxidants, radical scavengers, singlet quenchers, and ultraviolet absorbers, softeners, plasticizers, surface modifiers, extenders, thickeners, dispersion stabilizers, waxes, acceptors, and donors. A commonly known sensitizer such as terphenyl, a halonaphthoquinone, or acenaphthylene may be used in combination with the charge generating material in order to improve sensitivity of the photosensitive layer. A surfactant, a leveling agent, or the like may be used in order to improve dispersibility of the electron transport material or the charge generating material and to improve surface smoothness of the photosensitive layer.

(Manufacturing Method)

The single-layer electrophotographic photosensitive member can be manufactured by dissolving or dispersing the charge generating material, the hole transport material, the electron transport material, the binder resin, and, depending on necessity, various additives in a solvent, applying a resultant application liquid onto a conductive substrate, and drying the application liquid thereon. Although no particular limitations are placed on the application method, dip coating can for example be used as the application method.

Examples of various organic solvents that can be used as the aforementioned solvent include: alcohols such as methanol, ethanol, isopropanol, and butanol; aliphatic hydrocarbons such as n-hexane, octane, and cyclohexane; aromatic hydrocarbons such as benzene, toluene, and xylene; halogenated hydrocarbons such as dichloromethane, dichloroethane, chloroform, carbon tetrachloride, and chlorobenzene; ethers such as dimethyl ether, diethyl ether, tetrahydrofuran, ethylene glycol dimethyl ether, and diethylene glycol dimethyl ether; ketones such as acetone, methyl ethyl ketone, and cyclohexanone; esters such as ethyl acetate and methyl acetate; dimethyl formaldehyde; dimethyl formamide; and dimethyl sulfoxide. Any one type of the above solvents may be used or a combination of any two or more types of the above solvents may be used.

The amount of the triarylamine derivative according to the present disclosure represented by general formula (1) (hole transport material) is preferably at least 20 parts by mass and no greater than 500 parts by mass relative to 100 parts by mass of the binder resin, and more preferably at least 30 parts by mass and no greater than 200 parts by mass.

The amount of the charge generating material is preferably at least 0.1 parts by mass and no greater than 50 parts by mass relative to 100 parts by mass of the binder resin, and more preferably at least 0.5 parts by mass and no greater than 30 parts by mass.

In a situation in which an electron transport material is contained in the photosensitive layer, the amount of the electron transport material is preferably at least 5 parts by mass and no greater than 100 parts by mass relative to 100 parts by mass of the binder resin, and more preferably at least 10 parts by mass and no greater than 80 parts by mass.

The photosensitive layer of the single-layer electrophotographic photosensitive member has a thickness of at least 5 μm and no greater than 100 μm, and preferably at least 10 μm and no greater than 50 μm.

Figure 1B:
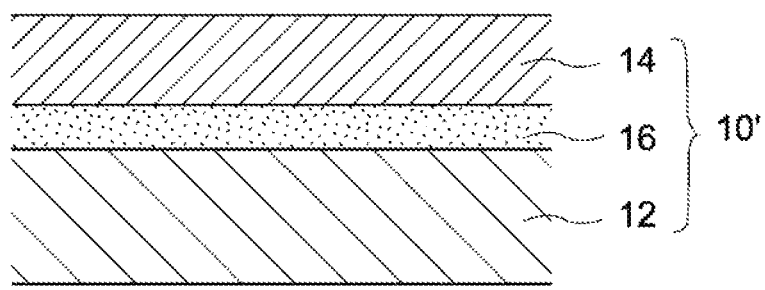
Figure 1C:
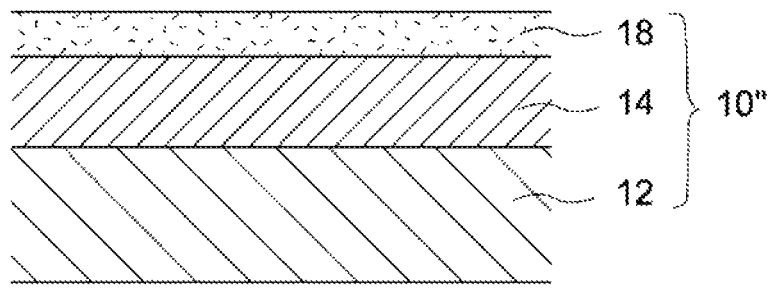

Note that the single-layer electrophotographic photosensitive member may alternatively be a photosensitive member 10' that includes a barrier layer 16 between a conductive substrate 12 and a photosensitive layer 14 as illustrated in FIG. 1B, so long as the barrier layer 16 does not hinder sensitivity properties of the single-layer electrophotographic photosensitive member. Further alternatively, the single-layer electrophotographic photosensitive member may be a photosensitive member 10" that includes a protective layer 18 on the surface of a photosensitive layer 14 as illustrated in FIG. 1C.

<<Multi-Layer Electrophotographic Photosensitive Member>>

Figure 2A:
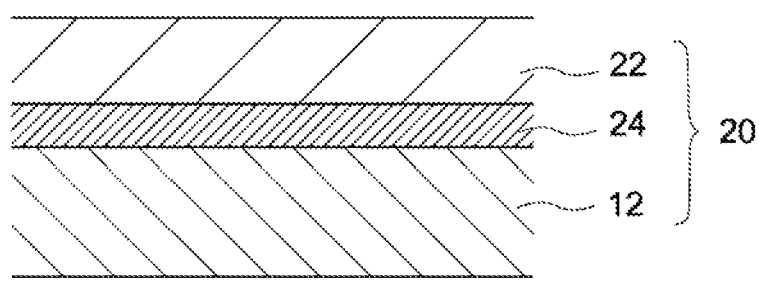
FIGS. 2A and 2B each illustrate a multi-layer electrophotographic photosensitive member according to an embodiment of the present disclosure.

As illustrated in FIG. 2A, a multi-layer electrophotographic photosensitive member 20 includes a conductive substrate 12, a charge generating layer 24 located on the conductive substrate 12, and a charge transport layer 22 located on the charge generating layer 24.

The multi-layer electrophotographic photosensitive member 20 is manufactured by forming the charge generating layer 24 containing the charge generating material on the conductive substrate 12 through a technique such as vapor deposition or coating, applying an application liquid including the triarylamine derivative represented by general formula (1) (hole transport material) and the binder resin onto the charge generating layer 24, and drying the application liquid to form the charge transport layer 22.

Figure 2B:
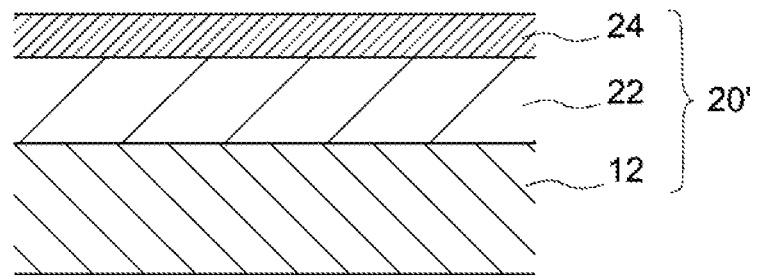

Alternatively, as illustrated in FIG. 2B, in a structure that is the reverse of that illustrated in FIG. 2A, the multi-layer electrophotographic photosensitive member may be a photosensitive member 20' including a conductive substrate 12, a charge transport layer 22 located on the conductive substrate 12, and a charge generating layer 24 located on the charge transport layer 22.

However, in consideration of the fact that the film thickness of the charge generating layer 24 is much thinner than that of the charge transport layer 22, the charge transport layer 22 is preferably located on the charge generating layer 24 as illustrated in FIG. 2A in order to protect the charge generating layer 24.

Note that materials such as the charge generating material, the hole transport material, the electron transport material, and the binder resin can be the same as described for the single-layer electrophotographic photosensitive member.

The multi-layer electrophotographic photosensitive member can be configured as a positively charging photosensitive member or a negatively charging photosensitive member in accordance with the order in which the charge generating layer 24 and the charge transport layer 22 are formed and with the type of charge transport material used in the charge transport layer 22. For example, in a configuration in which the charge generating layer 24 is located on the conductive substrate 12 and the charge transport layer 22 is located on the charge generating layer 24 as described above, the photosensitive member is negatively chargeable in a situation in which a hole transport material such as the triarylamine derivative according to the present disclosure represented by general formula (1) is used as the charge transport material contained in the charge transport layer 22. In the above configuration, the charge generating layer 24 may also contain an electron transport material.

The amount of the triarylamine derivative represented by general formula (1) (hole transport material) is preferably at least 10 parts by mass and no greater than 500 parts by mass relative to 100 parts by mass of the binder resin, and more preferably at least 25 parts by mass and no greater than 200 parts by mass.

The amount of the charge generating material is preferably at least 5 parts by mass and no greater than 1,000 parts by mass relative to 100 parts by mass of the binder resin contained in the charge generating layer, and more preferably at least 30 parts by mass and no greater than 500 parts by mass.

The amount of the charge transport material is preferably at least 10 parts by mass and no greater than 500 parts by mass relative to 100 parts by mass of the binder resin contained in the charge transport layer 22, and more preferably at least 25 parts by mass and no greater than 100 parts by mass.

The charge generating layer 24 preferably has a thickness of at least 0.01 μm and no greater than 5 μm, and more preferably at least 0.1 μm and no greater than 3 μm. The charge transport layer 22 preferably has a thickness of at least 2 μm and no greater than 100 μm, and more preferably at least 5 μm and no greater than 50 μm.

The electrophotographic photosensitive member according to the present disclosure can be used as an image bearing member in an electrophotographic image forming apparatus. No particular limitations are placed on the aforementioned image forming apparatus other than being an electrophotographic image forming apparatus. For example, the electrophotographic photosensitive member can be used as an image bearing member in an image forming apparatus such as an electrostatic copier, a facsimile machine, or a laser beam printer.

EXAMPLES

The following provides more specific explanation of the present disclosure through use of Examples. However, it should be noted that the present disclosure is not in any way limited by the Examples.

The following materials were synthesized or prepared in advance of carrying out the Examples and Comparative Examples.

[Synthesis of Compound 3a]

Compound 3a was prepared by carrying out a reaction represented by the reaction formula shown below.

Specifically, a 200 mL flask containing 16.1 g (0.1 mol) of compound 1a and 25 g (0.15 mol) of triethyl phosphite was stirred for 8 hours at 180° C.

Next, after cooling the flask to room temperature, excess triethyl phosphite was evaporated under reduced pressure to yield 24.1 g (percentage yield: approximately 92%) of the compound 3a (white liquid).

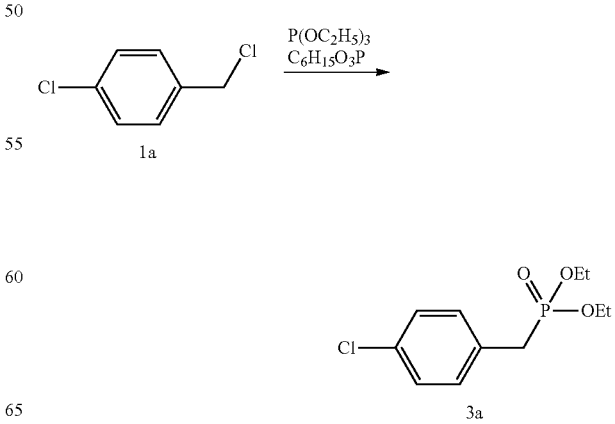

[Synthesis of Compound 5a]

Compound 5a was prepared by carrying out a reaction represented by the reaction formula shown below.

Specifically, a 500 mL two-necked flask containing 13 g (0.05 mol) of the prepared compound 3a was purged with argon gas and was stirred for 30 minutes at 0° C. after addition of 100 mL of dried tetrahydrofuran (THF) and 9.3 g (0.05 mol) of 28% sodium methoxide to the flask.

Next, the flask was stirred for a further 12 hours at room temperature after addition of 6.6 g (0.05 mol) of compound 4a dissolved in 300 mL of dried THF to the stirred liquid in the flask.

After stirring, the stirred liquid was poured into ion exchanged water and extraction was performed into toluene. The resultant organic layer was washed five times using ion exchanged water. Next, the organic layer was dried using anhydrous sodium sulfate and solvent was evaporated to leave a residue.

The resultant residue was purified by recrystallization using a mixed solvent of 20 mL of toluene and 100 mL of methanol to yield 10.8 g (percentage yield: approximately 90%) of the compound 5a (white crystals).

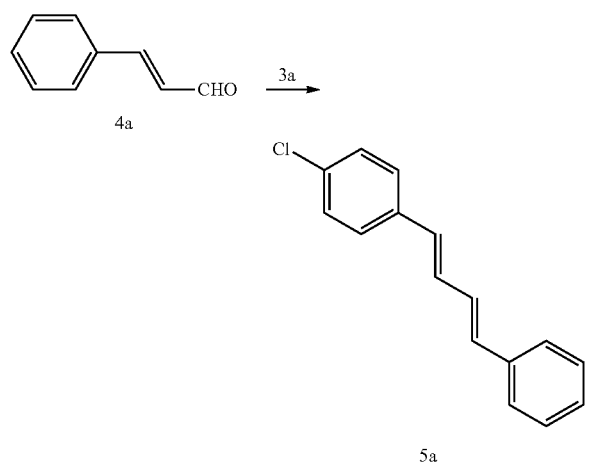

[Synthesis of Compound 5b]

Compound 5b was prepared by carrying out a reaction represented by the reaction formula shown below.

Specifically, a 500 mL two-necked flask containing 13 g (0.05 mol) of the prepared compound 3a was purged with argon gas and was stirred for 30 minutes at 0° C. after addition of 100 mL of dried tetrahydrofuran (THF) and 9.3 g (0.05 mol) of 28% sodium methoxide to the flask.

Next, the flask was stirred for a further 12 hours at room temperature after addition of 5 g (0.05 mol) of compound 4b dissolved in 300 mL of dried THF to the stirred liquid in the flask.

After stirring, the stirred liquid was poured into ion exchanged water and extraction was performed into toluene. The resultant organic layer was washed five times using ion exchanged water. Next, the organic layer was dried using anhydrous sodium sulfate and solvent was evaporated to leave a residue.

The resultant residue was purified by recrystallization using a mixed solvent of 20 mL of toluene and 100 mL of methanol to yield 9.3 g (percentage yield: approximately 92%) of the compound 5b (white crystals).

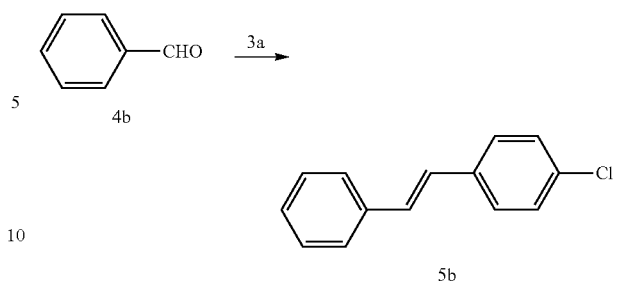

[Synthesis of Compound 5c]

Compound 5c was prepared by carrying out a reaction represented by the reaction formula shown below.

Specifically, a 500 mL two-necked flask containing 13 g (0.05 mol) of the prepared compound 3a was purged with argon gas and was stirred for 30 minutes at 0° C. after addition of 100 mL of dried tetrahydrofuran (THF) and 9.3 g (0.05 mol) of 28% sodium methoxide to the flask.

Next, the flask was stirred for a further 12 hours at room temperature after addition of 5.3 g (0.05 mol) of compound 4c dissolved in 300 mL of dried THF to the stirred liquid in the flask.

After stirring, the stirred liquid was poured into ion exchanged water and extraction was performed into toluene. The resultant organic layer was washed five times using ion exchanged water. Next, the organic layer was dried using anhydrous sodium sulfate and solvent was evaporated to leave a residue.

The resultant residue was purified by recrystallization using a mixed solvent of 20 mL of toluene and 100 mL of methanol to yield 11.0 g (percentage yield: approximately 90%) of the compound 5c (white crystals).

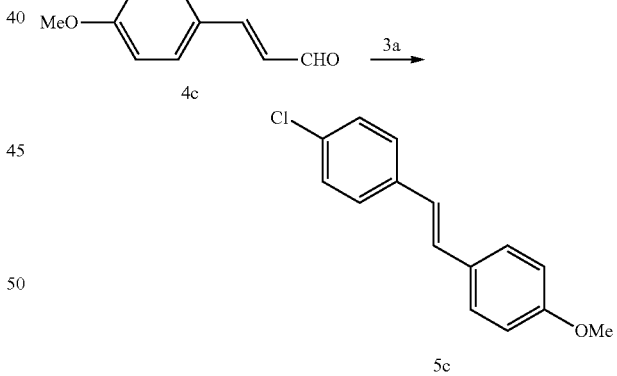

[Synthesis of Compound 5d]

Compound 5d was prepared by carrying out a reaction represented by the reaction formula shown below.

Specifically, a 500 mL two-necked flask containing 13 g (0.05 mol) of the prepared compound 3a was purged with argon gas and was stirred for 30 minutes at 0° C. after addition of 100 mL of dried tetrahydrofuran (THF) and 9.3 g (0.05 mol) of 28% sodium methoxide to the flask.

Next, the flask was stirred for a further 12 hours at room temperature after addition of 7.3 g (0.05 mol) of compound 4d dissolved in 300 mL of dried THF to the stirred liquid in the flask.

After stirring, the stirred liquid was poured into ion exchanged water and extraction was performed into toluene. The resultant organic layer was washed five times using ion exchanged water. Next, the organic layer was dried using anhydrous sodium sulfate and solvent was evaporated to leave a residue.

The resultant residue was purified by recrystallization using a mixed solvent of 20 mL of toluene and 100 mL of methanol to yield 10.8 g (percentage yield: approximately 85%) of the compound 5d (white crystals).

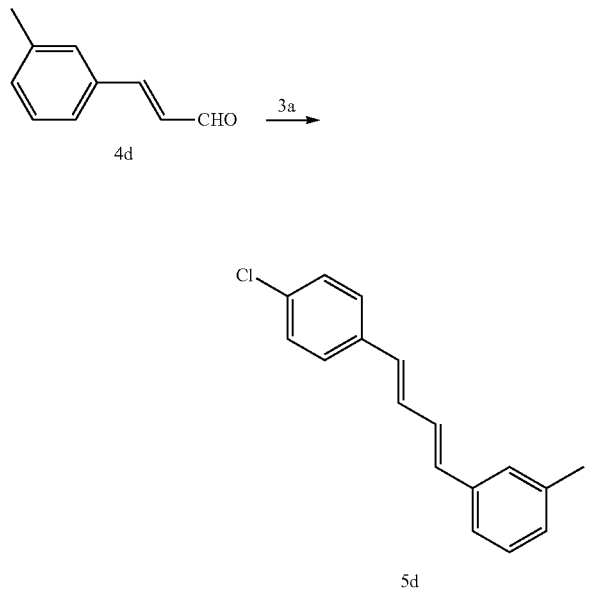

[Synthesis of Hole Transport Materials]

The triarylamine derivative represented by general formula (1) shown above was prepared as a hole transport material used in each of the Examples in accordance with hole transport material synthesis described above. In other words, triarylamine derivatives HT-1 to HT-6 described above were synthesized in accordance with synthesis examples 1-6 shown below. In addition, an amine stilbene derivative HT-A shown below was prepared as a hole transport material used in each of the Comparative Examples.

Synthesis Example 1

Synthesis of Triarylamine Derivative HT-1

The triarylamine derivative HT-1 was prepared by carrying out a two stage coupling reaction represented by reaction formula (1) shown below.

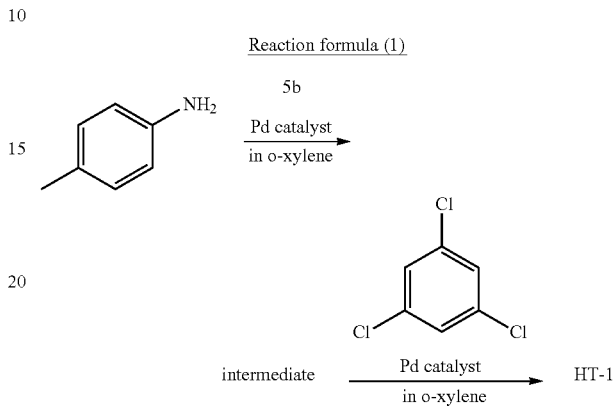

[First Coupling Reaction: Synthesis of Intermediate]

First, 100 mL of distilled o-xylene was added to a 2 L three-necked flask containing 4.4 g (0.020 mol) of the compound 5b, 0.072 g (0.0002049 mol) of tricyclohexylphosphine (PCy$_3$), 0.047 g (0.00005123 mol) of tris(dibenzylideneacetone)dipalladium (Pd$_2$(dba)$_3$), 2 g (0.021 mol) of sodium tert-butoxide (t-BuONa), and 2.14 g (0.020 mol) of p-toluidine. The flask was purged with argon gas and was then stirred for 5 hours at 120° C.

Next, the flask was cooled to room temperature. The resultant organic layer was washed three times with ion exchanged water and was subjected to drying and adsorption treatment using anhydrous sodium sulfate and activated clay. Subsequently, o-xylene was evaporated under reduced pressure to leave a residue.

The resultant residue was purified by silica gel column chromatography (developing solvent: chloroform/hexane) to yield 4.8 g (percentage yield: approximately 82%) of an intermediate.

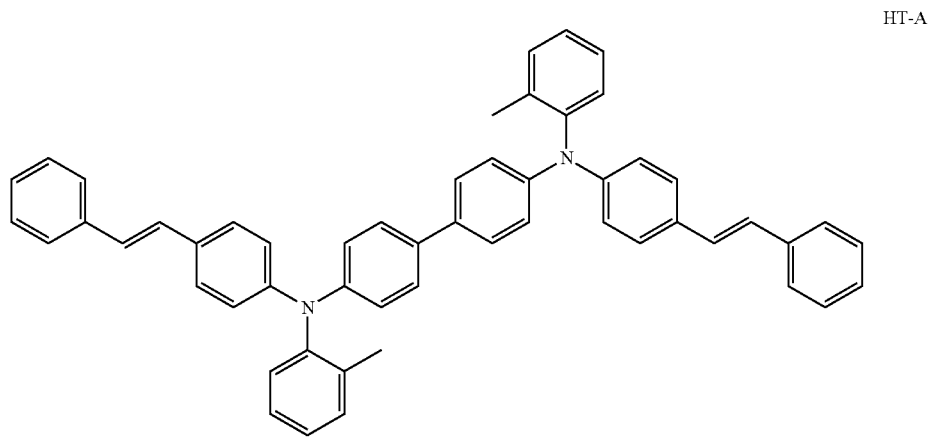 [SMILES: Cc1ccccc1N(c1ccc(/C=C/c2ccccc2)cc1)c1ccc(-c2ccc(N(c3ccc(/C=C/c4ccccc4)cc3)c3ccccc3C)cc2)cc1]

HT-A

[Second Coupling Reaction: Synthesis of Triarylamine Derivative HT-1]

First, 200 mL of distilled o-xylene was added to a 2 L three-necked flask containing 1.5 g (0.008 mol) of trichlorobenzene, 0.073 g (0.0002072 mol) of tricyclohexylphosphine (PCy$_3$), 0.076 g (0.00008287 mol) of tris(dibenzylideneacetone)dipalladium (Pd$_2$(dba)$_3$), 2.5 g (0.026 mol) of sodium tert-butoxide (t-BuONa), and 6.7 g (0.024 mol) of the intermediate. The flask was purged with argon gas and was then stirred for 5 hours at 120° C.

Next, the flask was cooled to room temperature. The resultant organic layer was washed three times with ion exchanged water and was subjected to drying and adsorption treatment using anhydrous sodium sulfate and activated clay. Subsequently, o-xylene was evaporated under reduced pressure to leave a residue.

Figure 3:
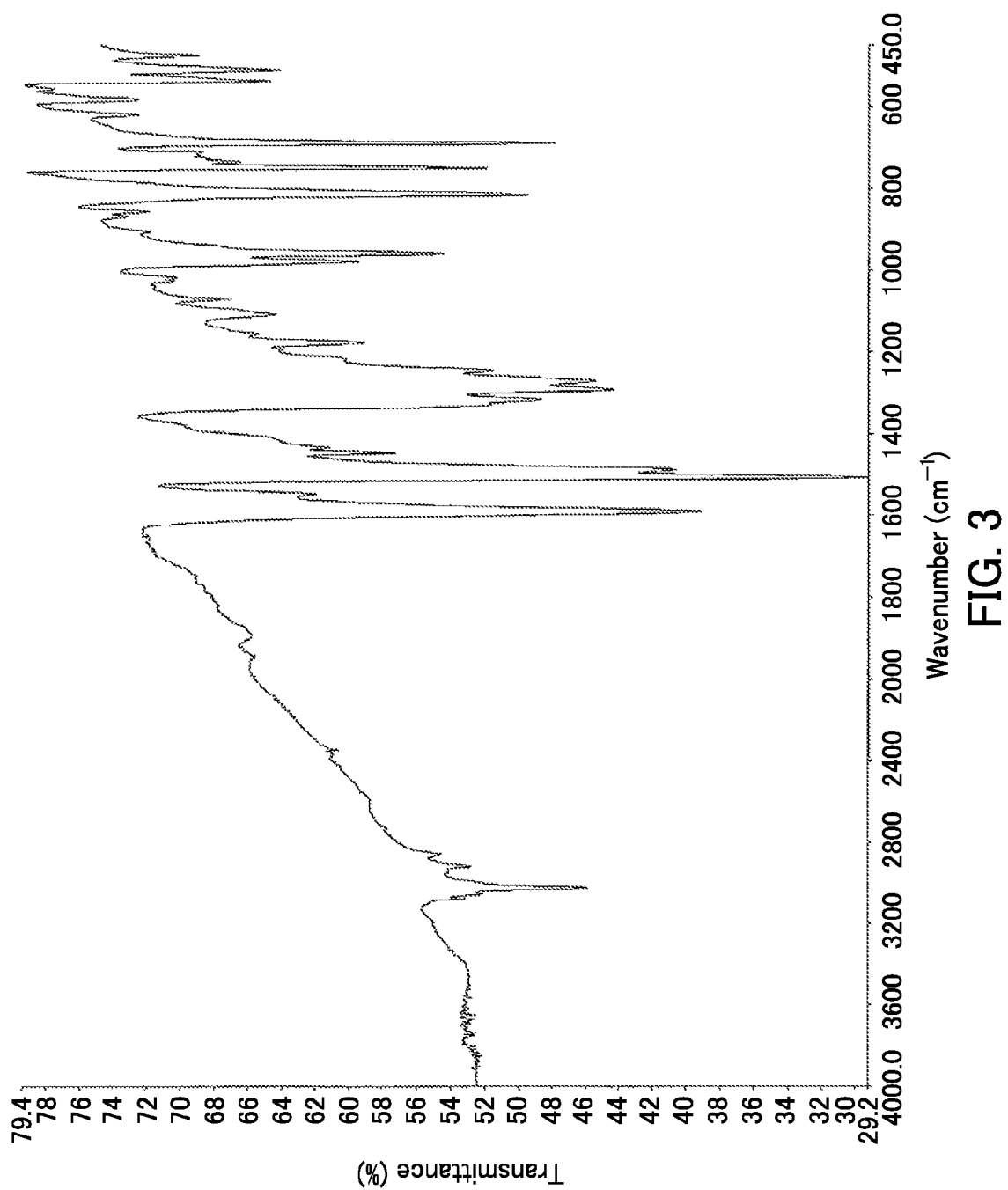
FIG. 3 is a graph illustrating an infrared absorption spectrum (IR spectrum) of a triarylamine derivative HT-1 according to an embodiment of the present disclosure.

The resultant residue was purified by silica gel column chromatography (developing solvent: chloroform/hexane) to yield a solid. The solid was analyzed by infrared spectroscopy (KBr pellet method). FIG. 3 illustrates an infrared absorption spectrum (IR spectrum) obtained by infrared spectroscopy. The IR spectrum was used to confirm that the resultant solid was the triarylamine derivative HT-1. The triarylamine derivative HT-1 (molecular weight 671.9) had a mass yield of 4.8 g (percentage yield: approximately 62%).

Synthesis Example 2

Synthesis of Triarylamine Derivative HT-2

The triarylamine derivative HT-2 was prepared by carrying out a two stage coupling reaction represented by reaction formula (2) shown below.

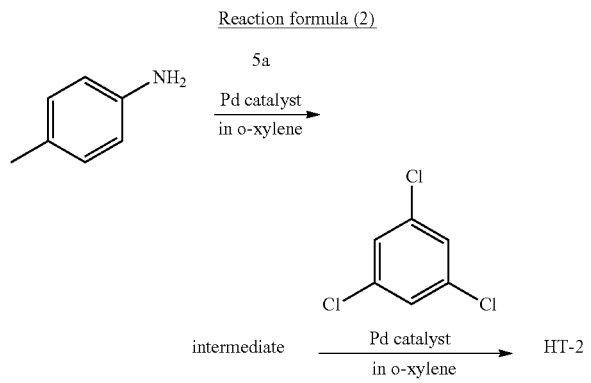

Reaction formula (2)

[First Coupling Reaction: Synthesis of Intermediate]

An intermediate was prepared in accordance with reaction formula (1) shown above, but using the compound 5a instead of the compound 5b.

Specifically, 100 mL of distilled o-xylene was added to a 2 L three-necked flask containing 4.81 g (0.02 mol) of the compound 5a, 0.072 g (0.0002049 mol) of tricyclohexylphosphine (PCy$_3$), 0.047 g (0.00005123 mol) of tris(dibenzylideneacetone)dipalladium (Pd$_2$(dba)$_3$), 2 g (0.021 mol) of sodium tert-butoxide (t-BuONa), and 2.14 g (0.020 mol) of p-toluidine. The flask was purged with argon gas and was then stirred for 5 hours at 120° C.

Next, the flask was cooled to room temperature. The resultant organic layer was washed three times with ion exchanged water and was subjected to drying and adsorption treatment using anhydrous sodium sulfate and activated clay. Subsequently, o-xylene was evaporated under reduced pressure to leave a residue.

The resultant residue was purified by silica gel column chromatography (developing solvent: chloroform/hexane) to yield 5.29 g (percentage yield: approximately 85%) of the intermediate.

[Second Coupling Reaction: Synthesis of Triarylamine Derivative HT-2]

First, 200 mL of distilled o-xylene was added to a 2 L three-necked flask containing 1.5 g (0.008 mol) of trichlorobenzene, 0.073 g (0.0002072 mol) of tricyclohexylphosphine (PCy$_3$), 0.076 g (0.00008287 mol) of tris(dibenzylideneacetone)dipalladium (Pd$_2$(dba)$_3$), 2.5 g (0.026 mol) of sodium tert-butoxide (t-BuONa), and 6.7 g (0.024 mol) of the intermediate. The flask was purged with argon gas and was then stirred for 5 hours at 120° C.

Next, the flask was cooled to room temperature. The resultant organic layer was washed three times with ion exchanged water and was subjected to drying and adsorption treatment using anhydrous sodium sulfate and activated clay. Subsequently, o-xylene was evaporated under reduced pressure to leave a residue.

Figure 4:
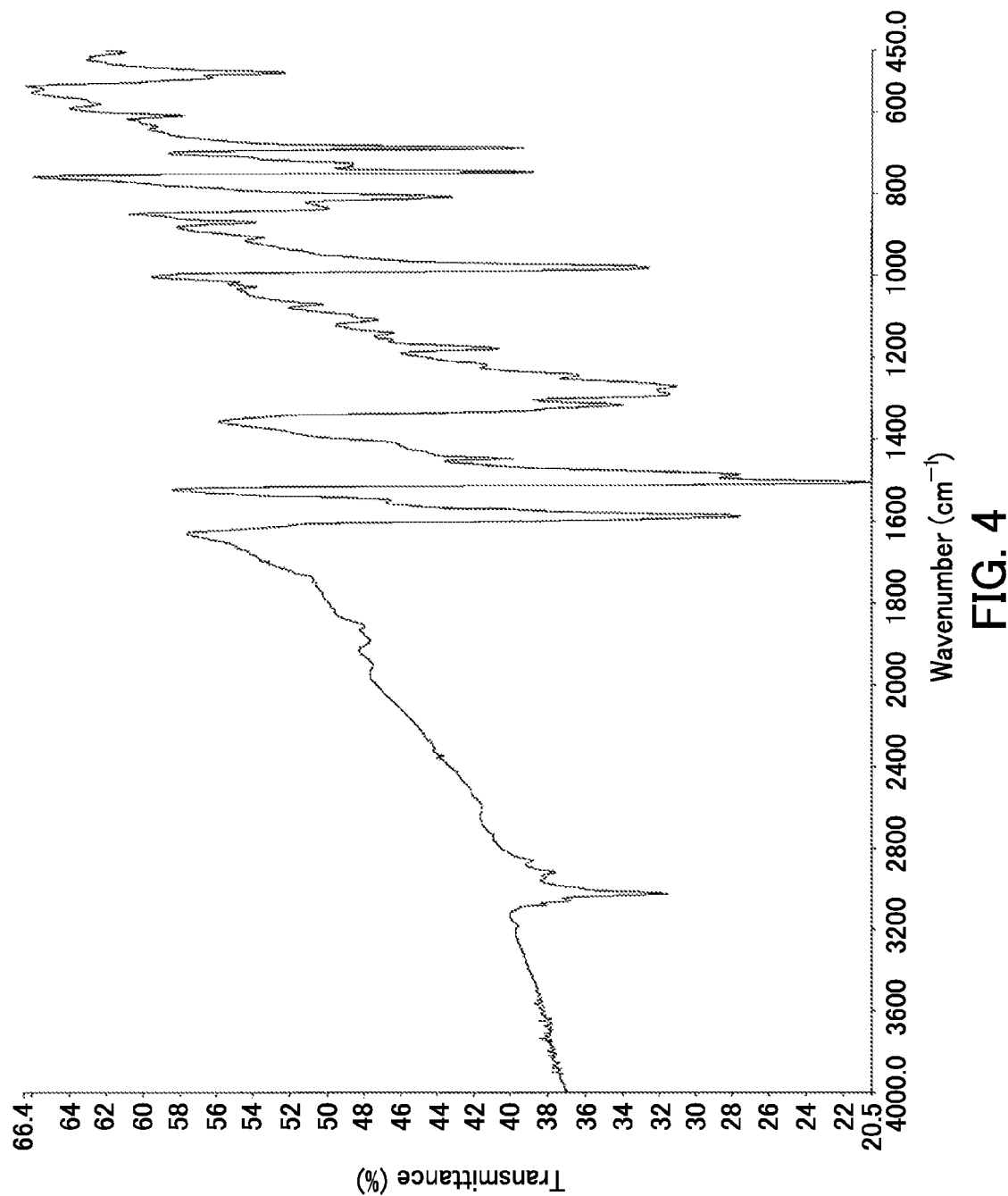
FIG. 4 is a graph illustrating an IR spectrum of a triarylamine derivative HT-2 according to an embodiment of the present disclosure.

The resultant residue was purified by silica gel column chromatography (developing solvent: chloroform/hexane) to yield a solid. The solid was analyzed by infrared spectroscopy (KBr pellet method). FIG. 4 illustrates an infrared absorption spectrum (IR spectrum) obtained by infrared spectroscopy. The IR spectrum was used to confirm that the resultant solid was the triarylamine derivative HT-2. The triarylamine derivative HT-2 (molecular weight 1,006) had a mass yield of 4.43 g (percentage yield: approximately 55%).

Synthesis Example 3

Synthesis of Triarylamine Derivative HT-3

The triarylamine derivative HT-3 was prepared by carrying out a two stage coupling reaction represented by reaction formula (3) shown below.

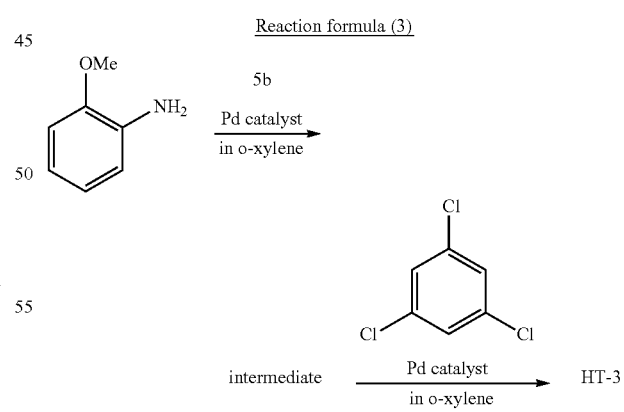

Reaction formula (3)

[First Coupling Reaction: Synthesis of Intermediate]

An intermediate was prepared in accordance with reaction formula (1) shown above, but using methoxyaniline instead of p-toluidine.

Specifically, 100 mL of distilled o-xylene was added to a 2 L three-necked flask containing 4.29 g (0.02 mol) of the compound 5b, 0.072 g (0.0002049 mol) of tricyclohexylphosphine (PCy$_3$), 0.047 g (0.00005123 mol) of tris(dibenzylideneacetone)dipalladium (Pd$_2$(dba)$_3$), 2 g (0.021 mol) of sodium tert-butoxide (t-BuONa), and 2.46 g (0.020 mol) of methoxyaniline. The flask was purged with argon gas and was then stirred for 5 hours at 120° C.

Next, the flask was cooled to room temperature. The resultant organic layer was washed three times with ion exchanged water and was subjected to drying and adsorption treatment using anhydrous sodium sulfate and activated clay. Subsequently, o-xylene was evaporated under reduced pressure to leave a residue.

The resultant residue was purified by silica gel column chromatography (developing solvent: chloroform/hexane) to yield 4.82 g (percentage yield: approximately 80%) of the intermediate.

[Second Coupling Reaction: Synthesis of Triarylamine Derivative HT-3]

First, 200 mL of distilled o-xylene was added to a 2 L three-necked flask containing 1.5 g (0.008 mol) of trichlorobenzene, 0.073 g (0.0002072 mol) of tricyclohexylphosphine (PCy$_3$), 0.076 g (0.00008287 mol) of tris(dibenzylideneacetone)dipalladium (Pd$_2$(dba)$_3$), 2.5 g (0.026 mol) of sodium tert-butoxide (t-BuONa), and 6.7 g (0.024 mol) of the intermediate. The flask was purged with argon gas and was then stirred for 5 hours at 120° C.

Next, the flask was cooled to room temperature. The resultant organic layer was washed three times with ion exchanged water and was subjected to drying and adsorption treatment using anhydrous sodium sulfate and activated clay. Subsequently, o-xylene was evaporated under reduced pressure to leave a residue.

The resultant residue was purified by silica gel column chromatography (developing solvent: chloroform/hexane) to yield 4.68 g (percentage yield: approximately 60%) of the triarylamine derivative HT-3.

Synthesis Example 4

Synthesis of Triarylamine Derivative HT-4

The triarylamine derivative HT-4 was prepared by carrying out a two stage coupling reaction represented by reaction formula (4) shown below.

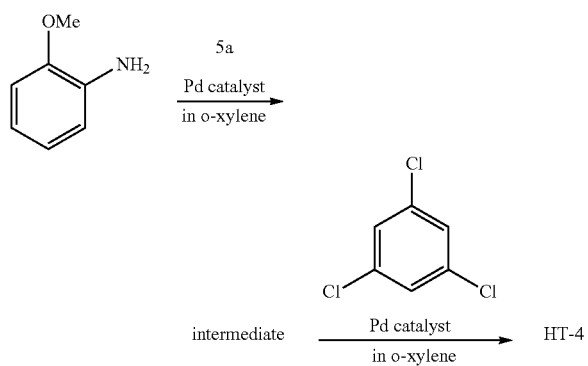

[First Coupling Reaction: Synthesis of Intermediate]

An intermediate was prepared in accordance with reaction formula (1) shown above, but methoxyaniline was used instead of p-toluidine and the compound 5a was used instead of the compound 5b.

Specifically, 100 mL of distilled o-xylene was added to a 2 L three-necked flask containing 4.81 g (0.02 mol) of the compound 5a, 0.072 g (0.0002049 mol) of tricyclohexylphosphine (PCy$_3$), 0.047 g (0.00005123 mol) of tris(dibenzylideneacetone)dipalladium (Pd$_2$(dba)$_3$), 2 g (0.021 mol) of sodium tert-butoxide (t-BuONa), and 2.46 g (0.020 mol) of methoxyaniline. The flask was purged with argon gas and was then stirred for 5 hours at 120° C.

Next, the flask was cooled to room temperature. The resultant organic layer was washed three times with ion exchanged water and was subjected to drying and adsorption treatment using anhydrous sodium sulfate and activated clay. Subsequently, o-xylene was evaporated under reduced pressure to leave a residue.

The resultant residue was purified by silica gel column chromatography (developing solvent: chloroform/hexane) to yield 5.23 g (percentage yield: approximately 80%) of the intermediate.

[Second Coupling Reaction: Synthesis of Triarylamine Derivative HT-4]

First, 200 mL of distilled o-xylene was added to a 2 L three-necked flask containing 1.5 g (0.008 mol) of trichlorobenzene, 0.073 g (0.0002072 mol) of tricyclohexylphosphine (PCy$_3$), 0.076 g (0.00008287 mol) of tris(dibenzylideneacetone)dipalladium (Pd$_2$(dba)$_3$), 2.5 g (0.026 mol) of sodium tert-butoxide (t-BuONa), and 6.7 g (0.024 mol) of the intermediate. The flask was purged with argon gas and was then stirred for 5 hours at 120° C.

Next, the flask was cooled to room temperature. The resultant organic layer was washed three times with ion exchanged water and was subjected to drying and adsorption treatment using anhydrous sodium sulfate and activated clay. Subsequently, o-xylene was evaporated under reduced pressure to leave a residue.

The resultant residue was purified by silica gel column chromatography (developing solvent: chloroform/hexane) to yield 4.64 g (percentage yield: approximately 55%) of the triarylamine derivative HT-4.

Synthesis Example 5

Synthesis of Triarylamine Derivative HT-5

The triarylamine derivative HT-5 was prepared by carrying out a two stage coupling reaction represented by reaction formula (5) shown below.

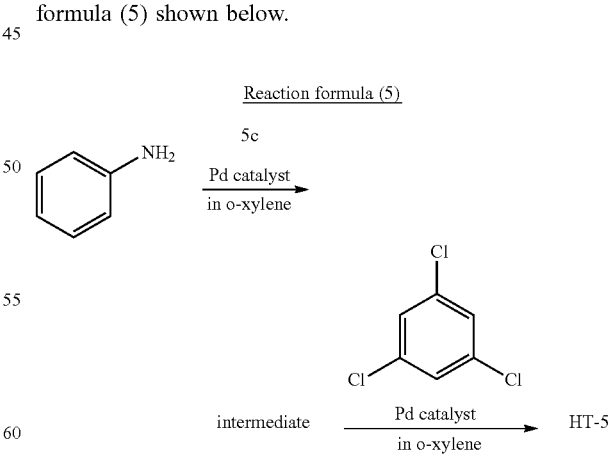

[First Coupling Reaction: Synthesis of Intermediate]

An intermediate was prepared in accordance with reaction formula (1) shown above, but aniline was used instead of p-toluidine and the compound 5c was used instead of the compound 5b.

Specifically, 100 mL of distilled o-xylene was added to a 2 L three-necked flask containing 4.89 g (0.02 mol) of the compound 5c, 0.072 g (0.0002049 mol) of tricyclohexylphosphine (PCy$_3$), 0.047 g (0.00005123 mol) of tris(dibenzylideneacetone)dipalladium (Pd$_2$(dba)$_3$), 2 g (0.021 mol) of sodium tert-butoxide (t-BuONa), and 1.86 g (0.020 mol) of aniline. The flask was purged with argon gas and was then stirred for 5 hours at 120° C.

Next, the flask was cooled to room temperature. The resultant organic layer was washed three times with ion exchanged water and was subjected to drying and adsorption treatment using anhydrous sodium sulfate and activated clay. Subsequently, o-xylene was evaporated under reduced pressure to leave a residue.

The resultant residue was purified by silica gel column chromatography (developing solvent: chloroform/hexane) to yield 4.94 g (percentage yield: approximately 82%) of the intermediate.

[Second Coupling Reaction: Synthesis of Triarylamine Derivative HT-5]

First, 200 mL of distilled o-xylene was added to a 2 L three-necked flask containing 1.5 g (0.008 mol) of trichlorobenzene, 0.073 g (0.0002072 mol) of tricyclohexylphosphine (PCy$_3$), 0.076 g (0.00008287 mol) of tris(dibenzylideneacetone)dipalladium (Pd$_2$(dba)$_3$), 2.5 g (0.026 mol) of sodium tert-butoxide (t-BuONa), and 6.7 g (0.024 mol) of the intermediate. The flask was purged with argon gas and was then stirred for 5 hours at 120° C.

Next, the flask was cooled to room temperature. The resultant organic layer was washed three times with ion exchanged water and was subjected to drying and adsorption treatment using anhydrous sodium sulfate and activated clay. Subsequently, o-xylene was evaporated under reduced pressure to leave a residue.

The resultant residue was purified by silica gel column chromatography (developing solvent: chloroform/hexane) to yield 4.68 g (percentage yield: approximately 60%) of the triarylamine derivative HT-5.

Synthesis Example 6

Synthesis of Triarylamine Derivative HT-6

The triarylamine derivative HT-6 was prepared by carrying out a two stage coupling reaction represented by reaction formula (6) shown below.

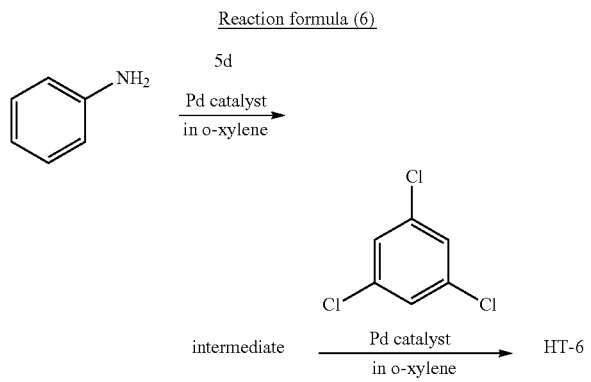

Reaction formula (6)

[First Coupling Reaction: Synthesis of Intermediate]

An intermediate was prepared in accordance with reaction formula (1) shown above, but aniline was used instead of p-toluidine and the compound 5d was used instead of the compound 5b.

Specifically, 100 mL of distilled o-xylene was added to a 2 L three-necked flask containing 5.10 g (0.02 mol) of the compound 5d, 0.072 g (0.0002049 mol) of tricyclohexylphosphine (PCy$_3$), 0.047 g (0.00005123 mol) of tris(dibenzylideneacetone)dipalladium (Pd$_2$(dba)$_3$), 2 g (0.021 mol) of sodium tert-butoxide (t-BuONa), and 1.86 g (0.020 mol) of aniline. The flask was purged with argon gas and was then stirred for 5 hours at 120° C.

Next, the flask was cooled to room temperature. The resultant organic layer was washed three times with ion exchanged water and was subjected to drying and adsorption treatment using anhydrous sodium sulfate and activated clay. Subsequently, o-xylene was evaporated under reduced pressure to leave a residue.

The resultant residue was purified by silica gel column chromatography (developing solvent: chloroform/hexane) to yield 4.98 g (percentage yield: approximately 80%) of the intermediate.

[Second Coupling Reaction: Synthesis of Triarylamine Derivative HT-6]

First, 200 mL of distilled o-xylene was added to a 2 L three-necked flask containing 1.5 g (0.008 mol) of trichlorobenzene, 0.073 g (0.0002072 mol) of tricyclohexylphosphine (PCy$_3$), 0.076 g (0.00008287 mol) of tris(dibenzylideneacetone)dipalladium (Pd$_2$(dba)$_3$), 2.5 g (0.026 mol) of sodium tert-butoxide (t-BuONa), and 6.7 g (0.024 mol) of the intermediate. The flask was purged with argon gas and was then stirred for 5 hours at 120° C.

Next, the flask was cooled to room temperature. The resultant organic layer was washed three times with ion exchanged water and was subjected to drying and adsorption treatment using anhydrous sodium sulfate and activated clay. Subsequently, o-xylene was evaporated under reduced pressure to leave a residue.

The resultant residue was purified by silica gel column chromatography (developing solvent: chloroform/hexane) to yield 4.59 g (percentage yield: approximately 57%) of the triarylamine derivative HT-6.

<<Preparation of Multi-Layer Electrophotographic Photosensitive Members>>

First, multi-layer electrophotographic photosensitive members of Examples and a Comparative Example were prepared and evaluated.

In other words, multi-layer electrophotographic photosensitive members of Examples 1-6 and Comparative Example 1 were prepared respectively using the triarylamine derivatives HT-1 to HT-6 and the amine stilbene derivative HT-A shown above as a hole transport material as shown below in Table 1.

Example 1

Intermediate Layer

An application liquid for intermediate layer formation was prepared by using a bead mill to disperse 2.8 parts by mass of titanium oxide subjected to surface treatment with alumina and silica, and subsequently with methyl hydrogen polysiloxane while in wet dispersion (test sample SMT-A produced by Tayca Corporation, number average primary particle size 10 nm), and 1 part by mass of copolyamide resin (DAIAMID X4685 produced by Daicel-Evonik Ltd.) in 10 parts by mass of ethanol and 2 parts by mass of butanol for 5 hours. The resultant application liquid for intermediate layer formation was filtered using a 5 micron filter, and was subsequently applied onto a conductive support—an aluminum drum-shaped support having a diameter of 30 mm and a total length of 238.5 mm—by dip coating and subjected to heat treatment for 30 minutes at 130° C. to form an intermediate layer having a film thickness of 1.5 μm.

(Charge Generating Layer)

An application liquid for charge generating layer formation was prepared by mixing 1 part by mass of Y-form titanyl phthalocyanine (Y-TiOPc) as a charge generating material, 1 part by mass of polyvinyl butyral resin (Denka Butyral 6000EP produced by Denki Kagaku Kogyo Kabushiki Kaisha) as a binder resin, and 40 parts by mass of propylene glycol monomethyl ether and 40 parts by mass of tetrahydrofuran as a dispersion medium, and dispersing the resultant mixture for two hours using a bead mill. The resultant application liquid for charge generating layer formation was filtered using a 3 micron filter, and was subsequently applied onto the intermediate layer prepared as described above by dip coating and dried for 5 minutes at 50° C. to form a charge generating layer having a film thickness of 0.3 μm.

(Charge Transport Layer)

An application liquid for charge transport layer formation was prepared by mixing and dissolving 70 parts by mass of the triarylamine derivative HT-1 shown above as a hole transport material, 5 parts by mass of BHT (2,6-di-tert-butyl-p-cresol) as an additive, 100 parts by mass of Z polycarbonate resin (TS2050 produced by Teijin Limited, viscosity average molecular weight 50,000) as a binder resin, and 430 parts by mass of tetrahydrofuran and 430 parts by mass of toluene as a solvent. The resultant application liquid for charge transport layer formation was filtered using a 3 micron filter, and was subsequently applied onto the charge generating layer prepared as described above and dried for 30 minutes at 130° C. to form a charge transport layer having a film thickness of 20 μm.

Through the above process, a multi-layer electrophotographic photosensitive member was prepared in which the intermediate layer, the charge generating layer, and the charge transport layer were formed in order on the conductive support.

Examples 2-6 and Comparative Example 1

Multi-layer electrophotographic photosensitive members were prepared in accordance with Example 1, but the triarylamine derivatives HT-2 to HT-6 and the amine stilbene derivative HT-A were used as the hole transport material instead of the triarylamine derivative HT-1 described above, as shown below in Table 1.

TABLE 1

| | Hole transport material | Crystallization evaluation | Charging potential ($V_0$) | Residual potential ($V_L$) |
| --- | --- | --- | --- | --- |
| Example 1 | HT-1 | Good | −700 | −103 |
| Example 2 | HT-2 | Good | −700 | −100 |
| Example 3 | HT-3 | Good | −700 | −105 |
| Example 4 | HT-4 | Good | −700 | −106 |
| Example 5 | HT-5 | Good | −700 | −106 |
| Example 6 | HT-6 | Good | −700 | −101 |
| Comparative Example 1 | HT-A | Good | −700 | −113 |

<<Evaluation>>

The multi-layer electrophotographic photosensitive member of each of Examples 1-6 and Comparative Example 1 was subjected to various evaluations in accordance with the standards shown below. Results of the evaluations are shown in Table 1.

(Crystallization Evaluation)

Crystallization at the surface of each of the prepared multi-layer electrophotographic photosensitive members was evaluated.

Specifically, presence of crystallization at the surface of the multi-layer electrophotographic photosensitive member was observed using an optical microscope and evaluated in accordance with the following standard.

Good: Crystallization observed

Mediocre: Slight crystallization observed

Poor: Crystallization not observed (Electrical Properties Evaluation)

Residual potential of each of the prepared multi-layer electrophotographic photosensitive members was evaluated.

Specifically, the surface potential of the prepared multi-layer electrophotographic photosensitive member was charged to −700 V ($V_0$) using a drum sensitivity test device (product of GENTEC Inc.). Next, a bandpass filter was used to obtain monochromatic light (half-width: 20 nm, light intensity: 0.4 μJ/m$^2$) having a wavelength of 780 nm from white light emitted by a halogen lamp. The surface of the multi-layer electrophotographic photosensitive member was irradiated with the monochromatic light for 1.5 seconds and a surface potential measured 0.5 seconds after irradiation was taken to be a residual potential ($V_L$).

The results in Table 1 demonstrate that Examples 1-6 including the triarylamine derivatives HT-1 to HT-6 represented by general formula (1) shown above as the hole transport material have higher sensitivity than Comparative Example 1 including the amine stilbene derivative HT-A as the hole transport material.

<<Preparation of Single-Layer Electrophotographic Photosensitive Members>>

Next, single-layer electrophotographic photosensitive members of Examples and Comparative Examples were prepared and evaluated.

The following materials were prepared in advance of carrying out the Examples and Comparative Examples.

[Charge Generating Materials]

The following charge generating materials were prepared.

X-form metal-free phthalocyanine (x-$H_2$Pc)

Y-form titanyl phthalocyanine (Y-TiOPc)

[Preparation of Electron Transport Materials]

Compounds ET-1 and ET-2 shown below were prepared as electron transport materials.

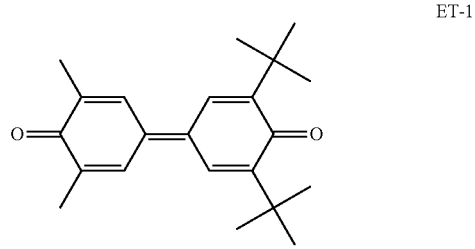

ET-1

-continued

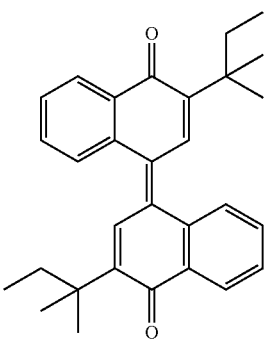
ET-2

As shown below in Table 2, single-layer electrophotographic photosensitive members of Examples 7-24 and Comparative Examples 2-4 were prepared using the triarylamine derivatives HT-1 to HT-6 and the amine stilbene derivative HT-A shown above as hole transport materials and using the compounds ET-1 and ET-2 shown above as electron transport materials.

Example 7

An application liquid for single-layer type photosensitive layer formation was prepared by using a ball mill to mix and disperse 5 parts by mass of X-form metal-free phthalocyanine as a charge generating material, 80 parts by mass of the triarylamine derivative HT-1 shown above as a hole transport material, 40 parts by mass of the compound ET-1 shown above as an electron transport material, and 100 parts by mass of a binder resin (polycarbonate) with 800 parts by mass of a solvent (tetrahydrofuran) for 50 hours. The resultant application liquid for single-layer type photosensitive layer formation was applied onto a conductive support—an aluminum drum-shaped support having a diameter of 30 mm and a total length of 238.5 mm—by dip coating and was subjected to hot-air drying for 30 minutes at 100° C. to prepare a single-layer electrophotographic photosensitive member having a single-layer type photosensitive layer thickness of 25 μm.

Examples 8-24 and Comparative Examples 2-4

Single-layer electrophotographic photosensitive members were prepared in accordance with Example 7 in all aspects other than that the charge generating material, the hole transport material, and the electron transport material were changed to the combinations shown below in Table 2.

TABLE 2

| | Charge generating material | Hole transport material | Electron transport material | Charging potential ($V_0$) | Residual potential ($V_L$) |
|---|---|---|---|---|---|
| Example 7 | X-form metal-free phthalocyanine | HT-1 | ET-1 | 701 | 108 |
| Example 8 | phthalocyanine | | ET-2 | 700 | 104 |
| Example 9 | Y-form titanyl phthalocyanine | | | 700 | 100 |
| Example 10 | X-form metal-free phthalocyanine | HT-2 | ET-1 | 700 | 105 |
| Example 11 | phthalocyanine | | ET-2 | 699 | 103 |
| Example 12 | Y-form titanyl phthalocyanine | | | 700 | 96 |
| Example 13 | X-form metal-free phthalocyanine | HT-3 | ET-1 | 700 | 109 |
| Example 14 | phthalocyanine | | ET-2 | 699 | 104 |
| Example 15 | Y-form titanyl phthalocyanine | | | 700 | 102 |
| Example 16 | X-form metal-free phthalocyanine | HT-4 | ET-1 | 700 | 108 |
| Example 17 | phthalocyanine | | ET-2 | 699 | 105 |
| Example 18 | Y-form titanyl phthalocyanine | | | 700 | 99 |
| Example 19 | X-form metal-free phthalocyanine | HT-5 | ET-1 | 700 | 108 |
| Example 20 | phthalocyanine | | ET-2 | 699 | 104 |
| Example 21 | Y-form titanyl phthalocyanine | | | 700 | 101 |
| Example 22 | X-form metal-free phthalocyanine | HT-6 | ET-1 | 700 | 106 |
| Example 23 | phthalocyanine | | ET-2 | 699 | 102 |
| Example 24 | Y-form titanyl phthalocyanine | | | 700 | 97 |
| Comparative Example 2 | X-form metal-free phthalocyanine | HT-A | ET-1 | 699 | 115 |
| Comparative Example 3 | | | ET-2 | 701 | 112 |
| Comparative Example 4 | Y-form titanyl phthalocyanine | | | 700 | 109 |

<<Evaluation>>

Electrical properties of the single-layer electrophotographic photosensitive members of Examples 7-24 and Comparative Examples 2-4 were evaluated according to the following standard. Results of the evaluations are shown in Table 2.

(Electrical Properties Evaluation)

Residual potential of each of the prepared single-layer electrophotographic photosensitive members was evaluated.

Specifically, the surface potential of the prepared single-layer electrophotographic photosensitive member was charged to +700 V ($V_0$) using a drum sensitivity test device (product of GENTEC Inc.). Next, a bandpass filter was used to obtain monochromatic light (half-width: 20 nm, light intensity: 1.5 μJ/m²) having a wavelength of 780 nm from white light emitted by a halogen lamp. The surface of the single-layer electrophotographic photosensitive member was irradiated with the monochromatic light for 1.5 seconds. A surface potential measured 0.5 seconds after irradiation was taken to be a residual potential ($V_L$).

The results shown above in Table 2 demonstrate that Examples 7-24 including the triarylamine derivatives HT-1 to HT-6, which are examples of the triarylamine derivative represented by general formula (1) shown above, as the hole transport material have higher sensitivity than Comparative Examples 2-4 including the amine stilbene derivative HT-A as the hole transport material.

What is claimed is:

1. A triarylamine derivative represented by general formula (1) shown below,

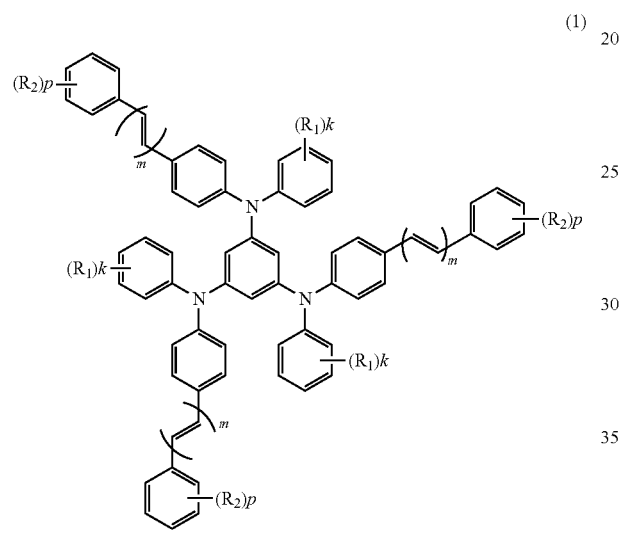

where, in the general formula (1), each $R_1$ independently represents a halogen atom, an optionally substituted alkyl group having a carbon number of at least 1 and no greater than 6, an optionally substituted alkoxy group having a carbon number of at least 1 and no greater than 6, or an optionally substituted aryl group having a carbon number of at least 6 and no greater than 12, each k independently represents an integer of at least 0 and no greater than 4, each m independently represents an integer of at least 1 and no greater than 3, each $R_2$ independently represents a halogen atom, an optionally substituted alkyl group having a carbon number of at least 1 and no greater than 6, an optionally substituted alkoxy group having a carbon number of at least 1 and no greater than 6, or an optionally substituted aryl group having a carbon number of at least 6 and no greater than 12, and each p independently represents an integer of at least 0 and no greater than 4.

2. The triarylamine derivative according to claim 1, wherein the triarylamine derivative is any one of triarylamine derivatives HT-1 to HT-6 shown below.

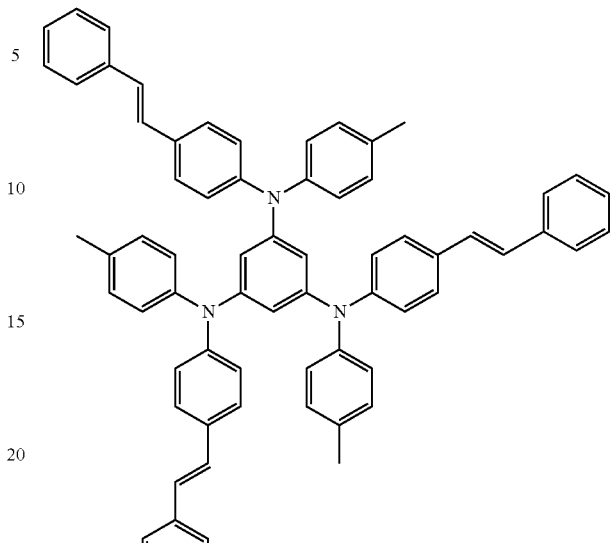

HT-1

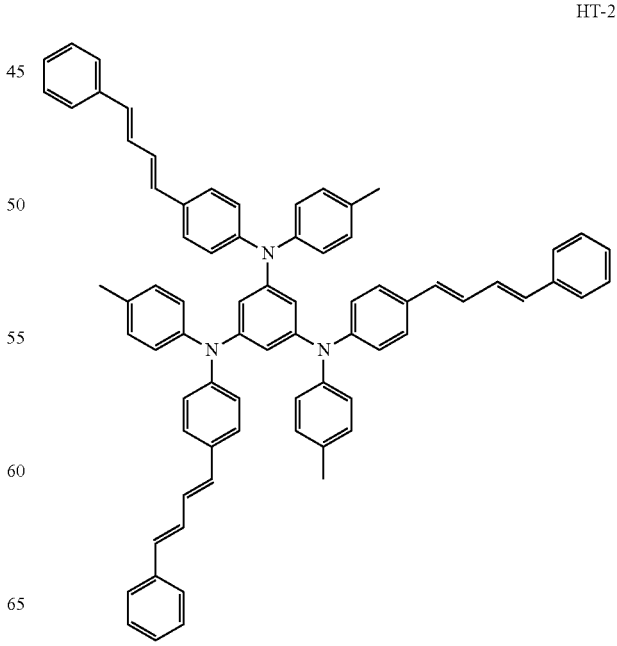

HT-2

-continued

HT-3

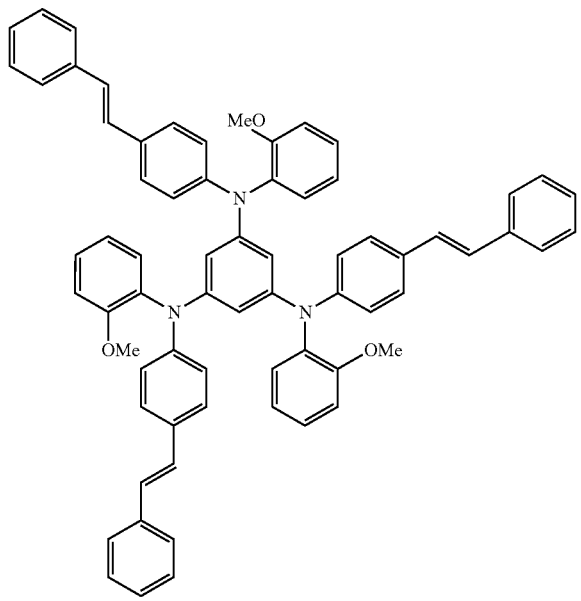

HT-4

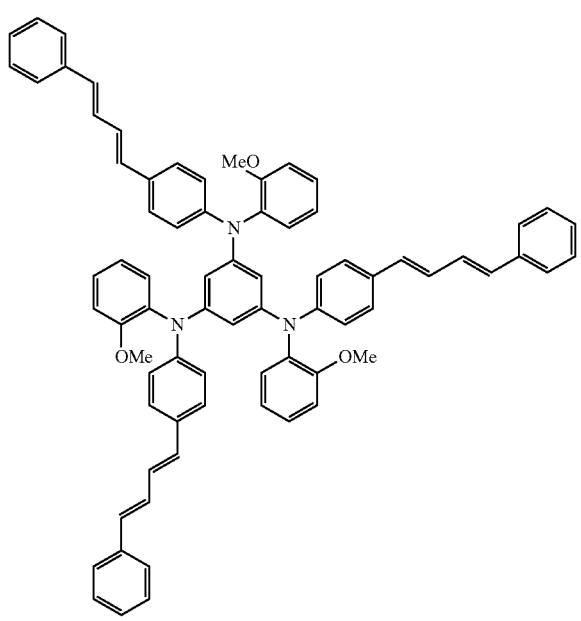

-continued

HT-5

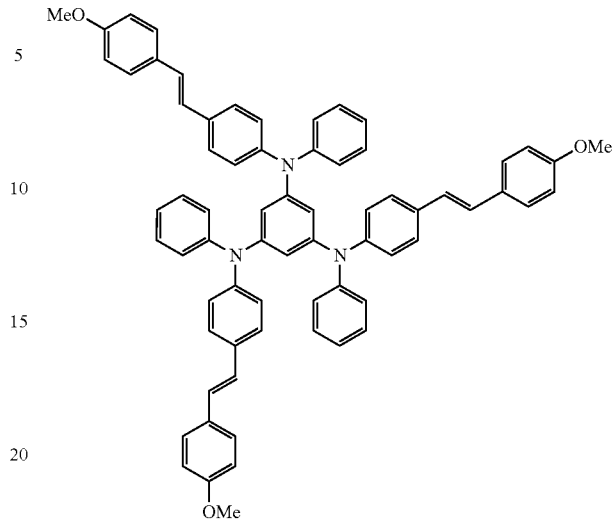

HT-6

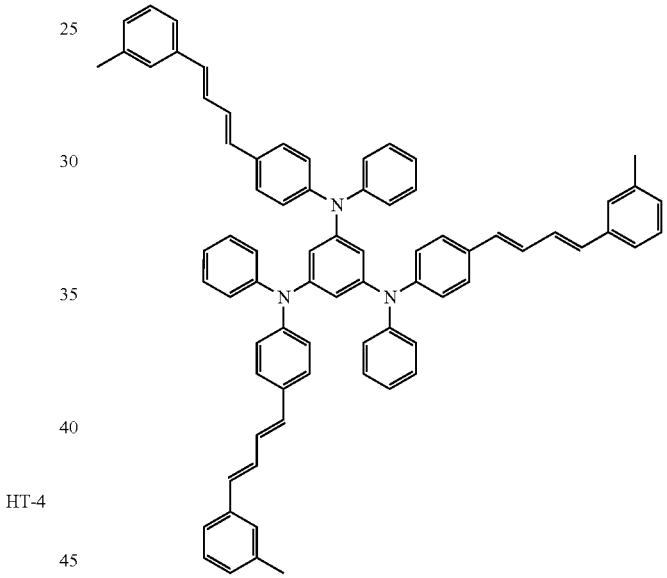

3. The triarylamine derivative according to claim 1, wherein
in the general formula (1), at least one $R_1$ or $R_2$ represents a methyl group.

4. An electrophotographic photosensitive member comprising
a conductive substrate and a photosensitive layer, wherein
the photosensitive layer contains the triarylamine derivative according to claim 1.

5. The electrophotographic photosensitive member according to claim 4 wherein
the photosensitive layer is a single-layer type photosensitive layer in which a charge generating material, a hole transport material, an electron transport material, and a binder resin are contained in the same layer as one another, and
the hole transport material includes the triarylamine derivative.

6. The electrophotographic photosensitive member according to claim 5, wherein the charge generating material includes Y-form titanyl phthalocyanine.

7. An electrophotographic photosensitive member comprising
a conductive substrate and a photosensitive layer, wherein
the photosensitive layer contains the triarylamine derivative according to claim 2.

8. The electrophotographic photosensitive member according to claim 7 wherein
the photosensitive layer is a single-layer type photosensitive layer in which a charge generating material, a hole transport material, an electron transport material, and a binder resin are contained in the same layer as one another, and
the hole transport material includes the triarylamine derivative.

9. The electrophotographic photosensitive member according to claim 8, wherein
the charge generating material includes Y-form titanyl phthalocyanine.

10. An electrophotographic photosensitive member comprising
a conductive substrate and a photosensitive layer, wherein
the photosensitive layer contains the triarylamine derivative according to claim 3.

11. The electrophotographic photosensitive member according to claim 10 wherein
the photosensitive layer is a single-layer type photosensitive layer in which a charge generating material, a hole transport material, an electron transport material, and a binder resin are contained in the same layer as one another, and
the hole transport material includes the triarylamine derivative.

12. The electrophotographic photosensitive member according to claim 11, wherein
the charge generating material includes Y-form titanyl phthalocyanine.

* * * * *